US012611724B2

(12) United States Patent
Cicchitti

(10) Patent No.: US 12,611,724 B2
(45) Date of Patent: Apr. 28, 2026

(54) METHOD OF MONITORING THE QUALITY OF ABSORBENT SANITARY ARTICLES, RELATED PRODUCTION LINE AND COMPUTER-PROGRAM PRODUCT

(71) Applicant: Fameccanica.Data S.p.A., San Giovanni Teatino (IT)

(72) Inventor: Anselmo Cicchitti, San Giovanni Teatino (IT)

(73) Assignee: Fameccanica.Data S.p.A., San Giovanni Teatino (IT)

( * ) Notice: Subject to any disclaimer, the term of this patent is extended or adjusted under 35 U.S.C. 154(b) by 1043 days.

(21) Appl. No.: 17/725,658

(22) Filed: Apr. 21, 2022

(65) Prior Publication Data

US 2022/0339729 A1     Oct. 27, 2022

(30) Foreign Application Priority Data

Apr. 23, 2021    (EP) ..................................... 21170055

(51) Int. Cl.
  *B23K 9/127*         (2006.01)
  *A61F 13/15*         (2006.01)
      (Continued)

(52) U.S. Cl.
  CPC ............ *B23K 9/127* (2013.01); *B23K 9/0953* (2013.01); *G06T 7/0004* (2013.01);
      (Continued)

(58) Field of Classification Search
  CPC .. B23K 9/127; B23K 9/0953; B23K 2103/38; G06T 7/0004; G06T 2207/20081;
      (Continued)

(56) References Cited

U.S. PATENT DOCUMENTS

2015/0374557 A1    12/2015  Varga et al.
2019/0340740 A1    11/2019  Li et al.

FOREIGN PATENT DOCUMENTS

CN      101304712 A    11/2008
CN      112285114 A     1/2021
WO    2007067103 A1     6/2007

OTHER PUBLICATIONS

Ander et al., NPL ("Spot Welding Monitoring System based on Fuzzy Classification and Deep Learning" Published 2017 by IEEE Total 6 Pages (Year: 2017).*

(Continued)

*Primary Examiner* — Quoc A Tran
(74) *Attorney, Agent, or Firm* — RMCK Law Group PLC

(57)                ABSTRACT

A method of analysing the quality of a welding area of an absorbent sanitary article is disclosed. During a learning step, a plurality of welding operations are performed both with a sufficient quality and with an insufficient quality, and the welding area generated for each welding operation is monitored via a camera. During a training step, the pixel data of the welding areas monitored during the learning step is processed for training a classifier configured to estimate a welding quality as a function of respective pixel data of a respective welding area. Accordingly, during a normal welding operating step, the welding quality may be estimate via the classifier, thereby improving the environmental sustainability of the production process.

11 Claims, 7 Drawing Sheets

(51) Int. Cl.

| | |
|---|---|
| *B23K 9/095* | (2006.01) |
| *B23K 103/00* | (2006.01) |
| *B29C 65/82* | (2006.01) |
| *G01N 21/89* | (2006.01) |
| *G01N 21/892* | (2006.01) |
| *G06N 3/08* | (2023.01) |
| *G06T 7/00* | (2017.01) |
| *G06T 7/11* | (2017.01) |
| *G06V 10/44* | (2022.01) |
| *G06V 10/70* | (2022.01) |
| *G06V 10/82* | (2022.01) |

(52) U.S. Cl.
CPC ............ *G06V 10/457* (2022.01); *G06V 10/82* (2022.01); *G06V 10/87* (2022.01); *A61F 13/15739* (2013.01); *A61F 13/15772* (2013.01); *A61F 2013/1578* (2013.01); *B23K 2103/38* (2018.08); *B29C 65/82* (2013.01); *G01N 21/8914* (2013.01); *G01N 21/892* (2013.01); *G06N 3/08* (2013.01); *G06T 7/11* (2017.01); *G06T 2207/20081* (2013.01); *G06T 2207/20084* (2013.01); *G06T 2207/20132* (2013.01); *G06T 2207/30124* (2013.01); *G06T 2207/30152* (2013.01)

(58) Field of Classification Search
CPC . G06T 2207/20084; G06T 2207/30124; G06T 7/11; G06T 2207/20132; G06T 2207/30152; G06V 10/457; G06V 10/82; G06V 10/87; B29C 65/82; G01N 21/8914; G01N 21/892; A61F 13/15739; A61F 2013/1578; A61F 13/15772; G06N 3/08

See application file for complete search history.

(56) References Cited

OTHER PUBLICATIONS

Luciane et al., NPL ("Seam Tracking and Welding Bead Geometry Analysis for Autonomous Welding Robot" Published 2017 by LARS Total 6 Pages (Year: 2017).*
European Search Report dated Oct. 6, 2021. 4 pages.
Chinese Office Action issued on Jun. 4, 2025.

* cited by examiner

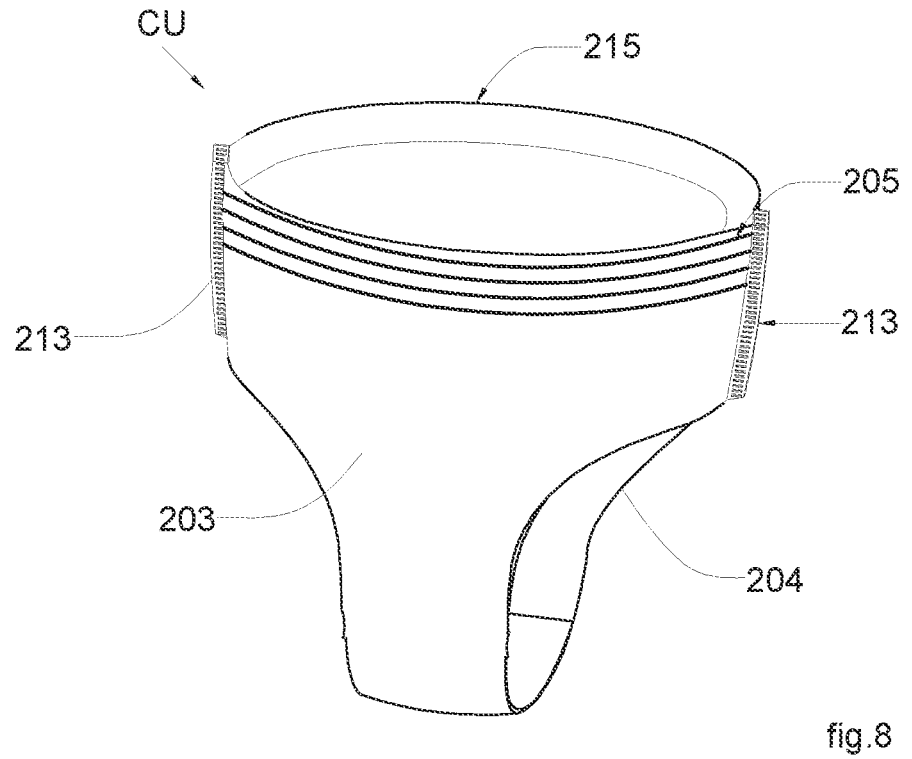
fig.8
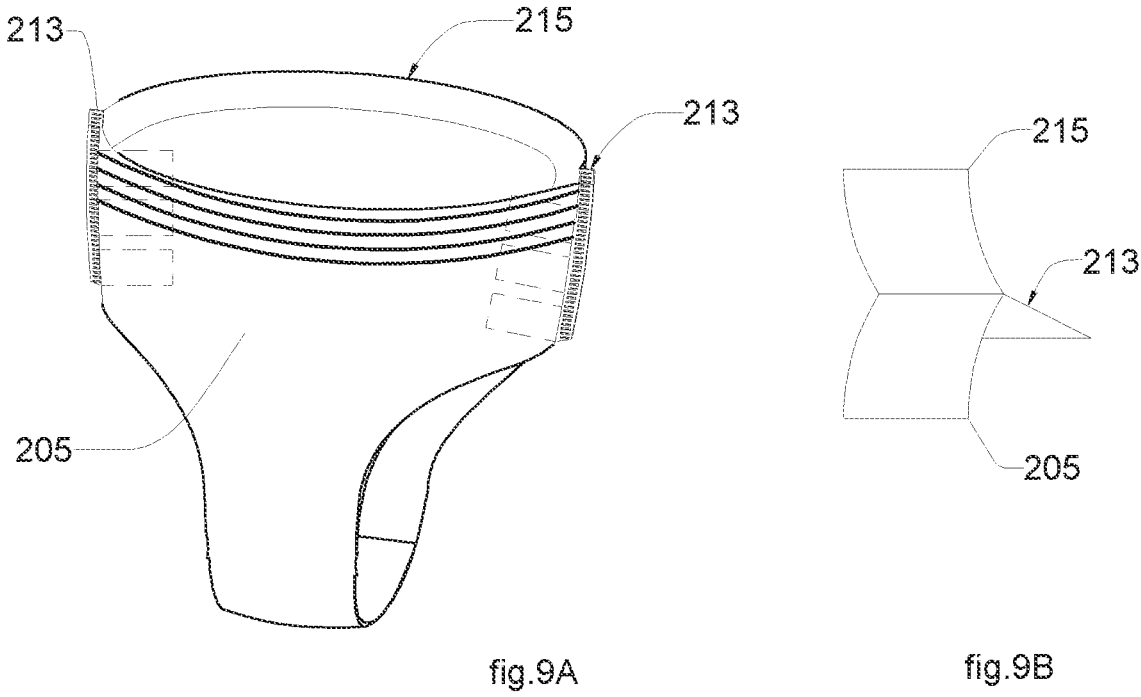
fig.9A
fig.9B

702

METHOD OF MONITORING THE QUALITY OF ABSORBENT SANITARY ARTICLES, RELATED PRODUCTION LINE AND COMPUTER-PROGRAM PRODUCT

CROSS-REFERENCE TO RELATED APPLICATION

This application claims priority to European Patent Application No. 21170055.4 filed Apr. 23, 2021. The disclosure of the above application is incorporated herein by reference in its entirety.

TECHNICAL FIELD

Method of monitoring the quality of absorbent sanitary articles, such as of diapers. For example, various embodiments relate to solutions for monitoring the quality of one or more weld areas of absorbent sanitary articles.

BACKGROUND

Absorbent sanitary articles, such as diapers for babies, also including the so called "training pants", or incontinence pads for adults, are well known in the art. For example, in this context may be cited United States Patent Publication No. U.S. Pat. No. 6,572,595 B1 or European Patent No. EP 1 842 516 B1.

In the field of production of such absorbent sanitary articles, it is frequently necessary to perform one or more transverse and/or longitudinal welding operations on composite layers of materials, e.g., in order to enclose an absorbent core and/or to fix further elements to a central portion typically comprising the absorbent core. For example, for this purpose, the composite layers may advance as tapes in a machine direction. The continuous composite tape is then welded at regular intervals, e.g., to form closure lines.

For example, as disclosed in United States Patent Publication No. U.S. Pat. No. 10,894,386 B2, typically two technologies are used to weld the component materials used in the absorbent sanitary articles: thermal welding and ultrasonic welding. In order to execute the welding lines on composite tapes, the welding elements remain in contact with the tape for the time necessary to transfer the welding energy from the welding elements to the moving tape. In the case of thermal welding, the moving tape is typically clamped between two heated welding elements. In the case of ultrasonic welding, the moving tape is clamped between a sonotrode and an anvil.

For example, as schematically shown in FIG. 1, an apparatus for producing absorbent sanitary article 10 may comprise a welding unit 12 including an anvil roller 16 rotatable about the longitudinal axis and a welding element 18 cooperating with the anvil roller 16. In the example illustrated in FIG. 1, the welding element 18 is a sonotrode of an ultrasonic welding device.

In order to implement the above cited welding patterns, the outer surface of the anvil roller 16 may comprise a plurality of protrusions 20 formed by small pins having head surfaces which cooperate with the sonotrode 18 to form ultrasonic welding points on a moving web W. The head surfaces of the protrusions 20 may have any shape, such as, for example, circular or polygonal (e.g., rhomboidal). The protrusions 20 are arranged on the outer surface of the anvil roller 16 so as to define the welding pattern which corresponds to the distribution of the welding points on the moving web. In case of a thermo-mechanical welding unit 12, the sonotrode 18 would be replaced by a heated welding roller pressed on the outer surface of the anvil roller 16. Generally, the protrusions 20 may be arranged according to any desired profile, e.g., may be arranged along a series of sinusoidal lines, i.e., the shape of the welding pattern may vary according to the desired aesthetic effect on the web surface.

In the example considered, the apparatus 10 comprises an inlet roller 24 which guides a composite (elastic or non-elastic) web W onto the outer surface of the anvil roller 16. The web W is retained on the outer surface of the anvil roller 16 and as a result of the rotation of the anvil roller 16, passes through the welding area 34 formed by the outer surface of the anvil roller 16 and the sonotrode 18 or, alternatively, between the contact surfaces between the anvil roller 16 and the welding roller in the case of thermo-mechanical welding. The composite web W is formed of a plurality of layers coupled together. For example, in FIG. 1 is shown that the web W may comprise two outer layers of non-woven fabric NW1, NW2 and an optional internal layer EF enclosed between the two layers of fabric NW1, NW2. For example, for this purpose, the apparatus 10 may comprise a feeding assembly 26 arranged to feed the layers that comprise the web W to the inlet roller 24. In the example illustrated in FIG. 1, the feeding assembly 26 may comprise a plurality of pairs of rollers 28, 30, 32 which feed, respectively, the two layers of non-woven fabric NW1, NW2 and the internal layer EF. For example, the internal layer may be an elastic layer, e.g., having applied thereto the absorbent core. However, the absorbent core may also be applied to one of the layers NW1 or NW2. FIG. 1 also shows a release roller 40 arranged downstream of the welding area 34, which detaches the web W from the outer surface of the anvil roller 16.

Generally, such welding operations may also be used for other purposes and/or while the web composite material is advancing in a linear direction. In fact, in general such welding operations are used to fix a first layer to a second layer. For example, European Patent Application Nr. EP 3 583 929 A1 discloses a welding operation in order to implement "training pants".

Modern machines for producing absorbent sanitary articles operate at extremely high speeds, e.g., in the order of 800-1000 pieces/1'. This speed of production renders an online quality control rather complex.

Accordingly, typically random products are selected periodically and one or more test are performed on the absorbent sanitary article. For example, these tests may include mechanical tests in order to determine the quality of the welding operation. For example, concerning possible test procedures for composite materials, reference may be made, e.g., to the standards ISO 527-1 and 527-4.

However, in case such tests show that the product quality is insufficient, e.g., due to a malfunction or wear of the welding element 18, indeed a significant number of products may already have been produced. Accordingly, a significant number of products may be defect, thus increasing the costs of the production and creating unnecessary waste, with evident negative impact on the environmental sustainability of the production process.

SUMMARY

The object of various embodiments of the present disclosure relates to solutions for monitoring in real-time the quality of the welding operation of absorbent sanitary articles.

According to one or more embodiments, one or more of the objects referred to are achieved via a method having the distinctive elements set forth specifically in the ensuing claims. The embodiments moreover regard a corresponding production line, as well as a corresponding computer-program product that can be loaded into the memory of at least one computer and comprises portions of software code for implementing the steps of the method when the product is run on a computer. As used herein, reference to such a computer-program product is intended as being equivalent to reference to a computer-readable medium containing instructions for controlling a computing system in order to co-ordinate execution of the method. Reference to "at least one computer" is intended to highlight the possibility of the present invention being implemented in a distributed/modular way.

The claims form an integral part of the technical teaching of the disclosure provided herein.

BRIEF DESCRIPTION OF THE DRAWINGS

The embodiments of the present disclosure will now be described with reference to the annexed drawings, which are provided purely by way of non-limiting example and in which:

FIG. 8 shows an embodiment of a sanitary article;

FIGS. 9A and 9B show an embodiment of a test used to determine the quality of a weld area.

DETAILED DESCRIPTION

Figure 1:
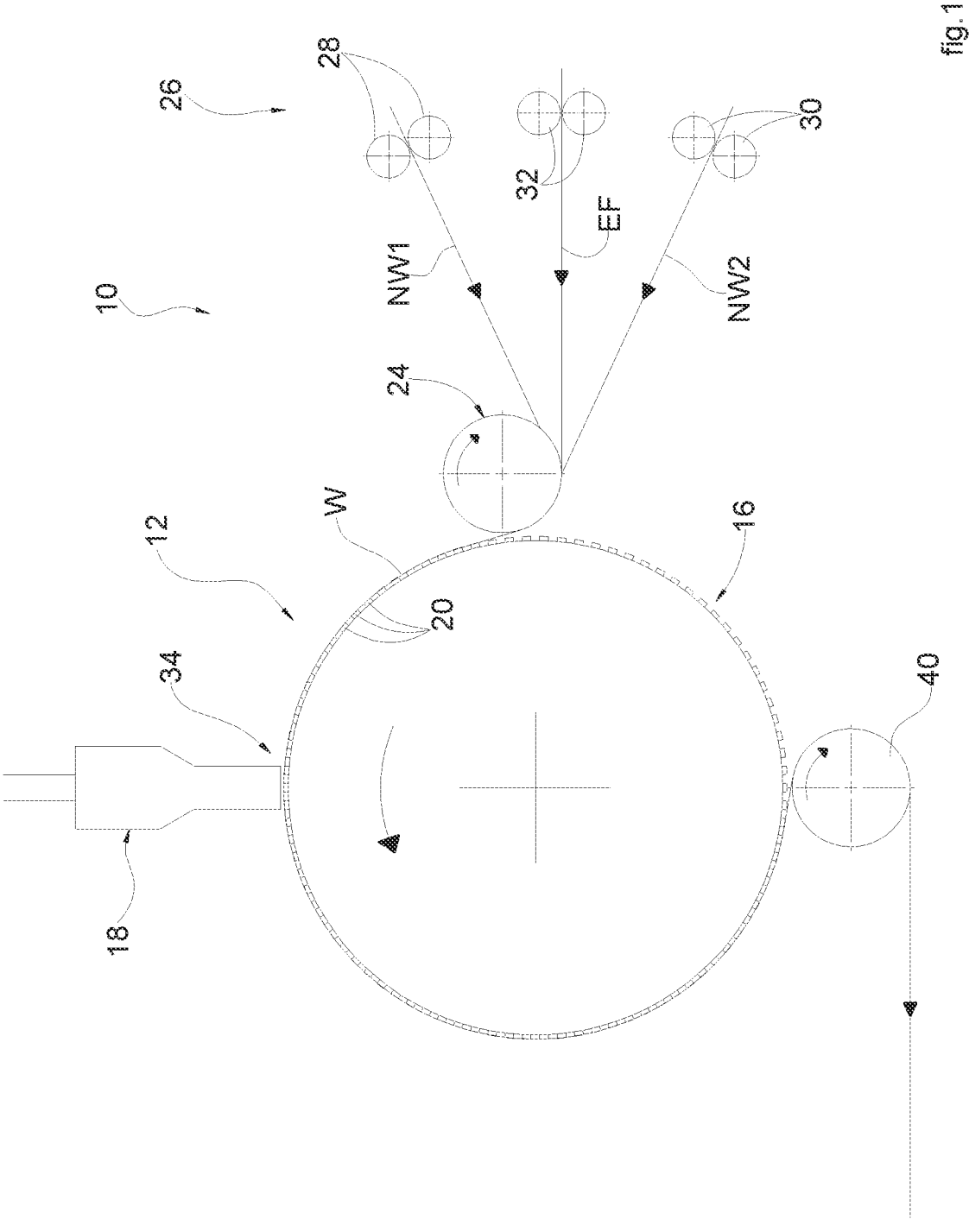
FIG. 1 shows an example of a welding station for absorbent sanitary articles.

In the ensuing FIGS. 2 to 10, the parts, elements, or components that have already been described with reference to FIG. 1 are designated by the same references used previously in the above figures. The aforesaid elements described previously will not be described again hereinafter in order not to overburden the present detailed description.

As mentioned before, the present description provides solutions for monitoring the quality of a welding operation of absorbent sanitary articles.

Figure 2:
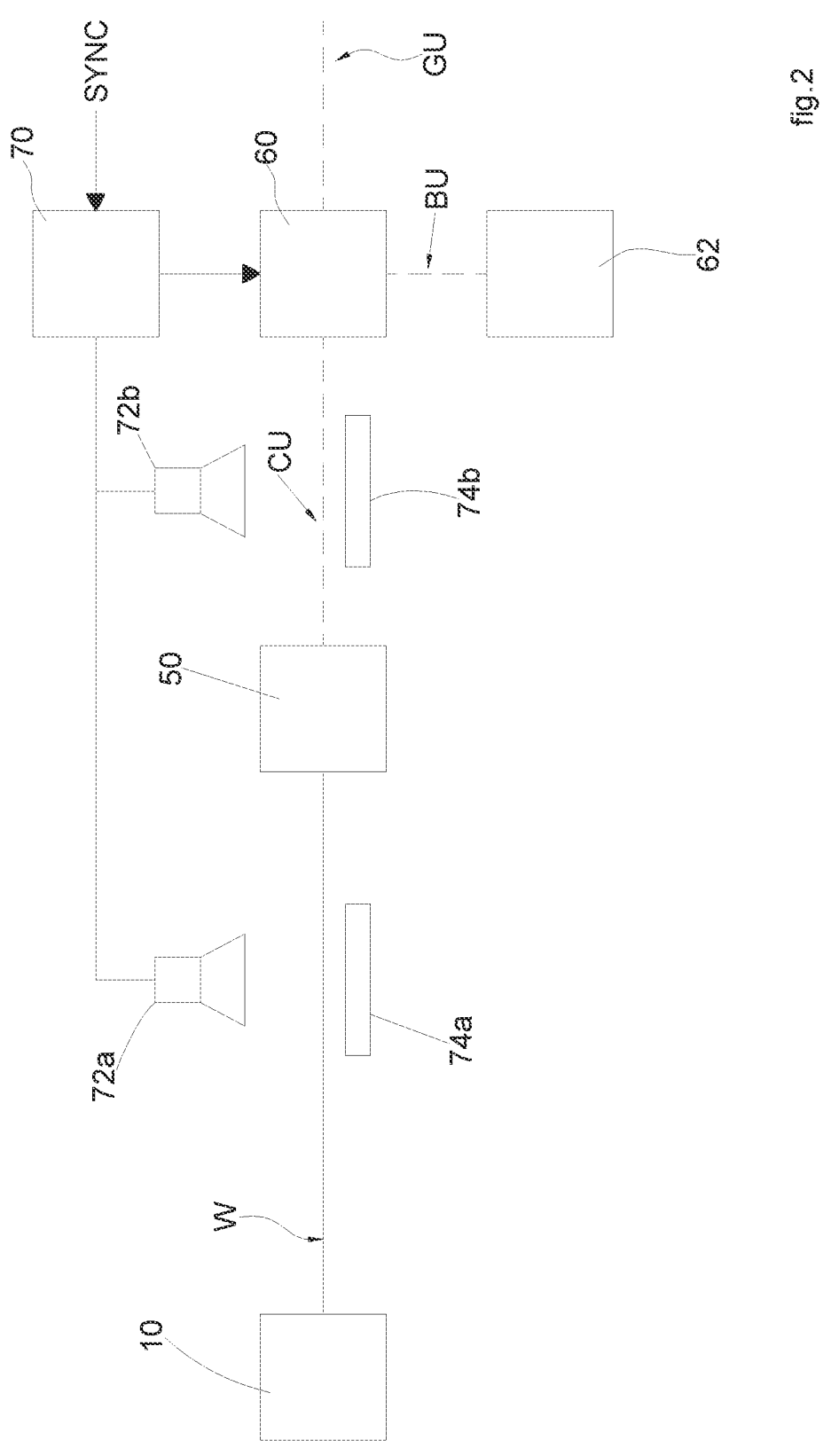
FIG. 2 shows an embodiment of a production line for absorbent sanitary articles.

For example, FIG. 2 schematically shows a production line for producing absorbent sanitary articles, such as diapers for babies, also including the so called "training pants", or incontinence pads for adults.

In the embodiment considered, the production line comprises one or more welding stations 10, which apply one or more welding operations to a web W of a composite material comprising a sequence of product units, thereby forming a weld pattern in one or more weld areas. For a possible embodiment of such welding stations, reference can be made to the description of FIG. 1.

Figure 3:
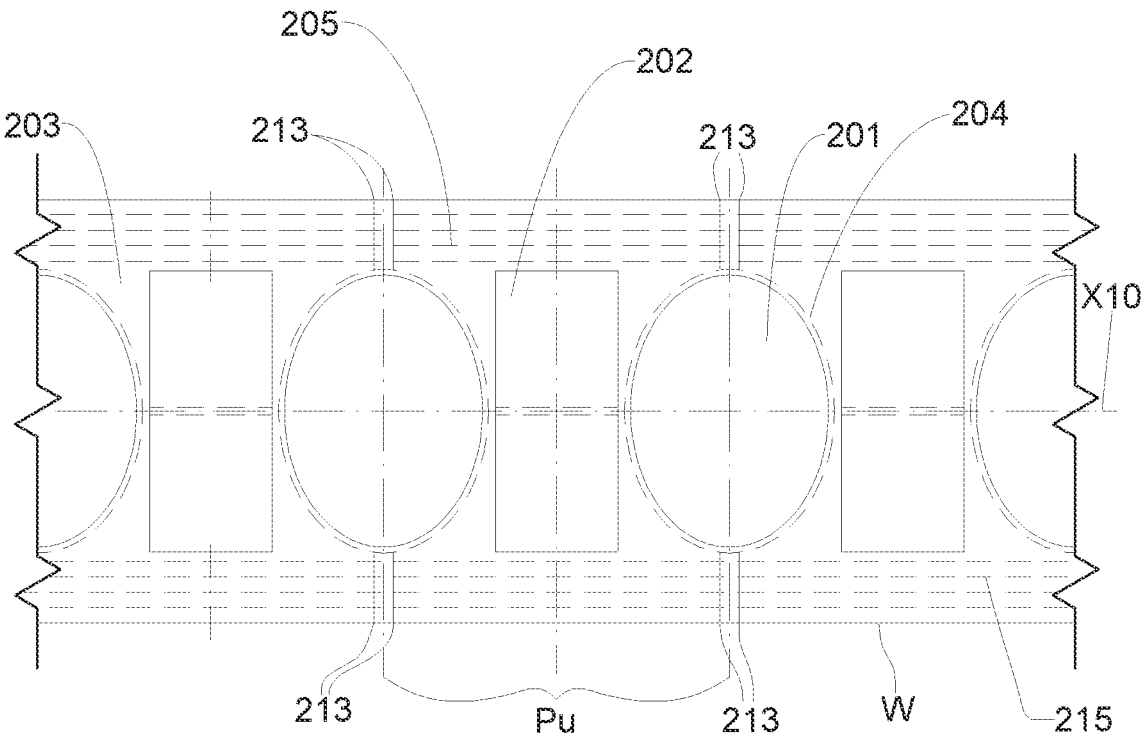
FIG. 3 shows an example of a composite web formed of semi-finished blanks.

For example, FIG. 3 shows an embodiment of a web W in accordance with United States Patent Publication nr. U.S. Pat. No. 10,377,085 B2. Specifically, in FIG. 3, the web W comprises:

a first or front waist region 205;

a second or rear waist region 215;

a crotch region 203 located between the two waist regions 205, 215;

a series of cuts 204, each of which contributes to define the contour of openings for legs 201 of two consecutive product units PU;

an absorbent insert 202, which is placed between two consecutive cuts 204; and a transverse axis X10 equidistant from the end edges of the two waist regions 205 and 215.

In case of diapers, each product unit PU is typically defined by welding lines 213, wherein each product unit PU comprises two welding lines 213 in the region 205 and two welding lines 213 in the region 215. Conversely, in case of training pants, in order to assume its pant configuration, the absorbent article is typically folded about its transverse axis X10, overlapping the two waist regions 205 and 215, and two welding lines 213 are applied in the overlapping region 205/215.

Typically, the web W is then provided to a cutting station 50, which cuts the web W at given positions, in particular between the product units PU, thereby implementing cut product units CU. For example, typically the cutting station 50 cuts the web W between two consecutive welding lines 213.

Generally, further operations may be performed:

between the welding stations of a plurality of welding stations 10; and/or between the last welding station 10 and the cutting unit 50; and/or downstream the cutting unit 50.

For example, such further operations may include fold operations, operations for applying adhesive tapes, etc.

Even though modern welding stations meet stringent criteria of quality and stability over time, a verification of the quality of the welding operation may be required.

The person skilled in the art will appreciate that for a continuous or at least periodical monitoring of the weld-spot quality a non-destructive testing method is preferable. In particular, such non-destructive tests are experimental investigations aimed at identifying and characterizing insufficient weld spots that might potentially jeopardize the performance thereof in the end product. The point in common with non-destructive testing techniques is hence their capacity not to affect in any way the chemical, physical, and functional characteristics of the object under analysis.

Accordingly, as shown in FIG. 2, in various embodiments, the production line comprises also a quality control system. Specifically, the quality control system comprises at least one camera 72 and a processing unit 70, such as a computer programmed via software instructions, configured to elaborate the images provided by the camera 72 in order classify the quality of a product unit, in particular with respect to the quality of one or more of the weld areas.

Generally, the camera 72 may correspond to:

a camera 72a placed upstream of the cutting unit 50, e.g., at the output of a given welding station 10, and/or a camera 72b placed downstream of the cutting unit 50.

Accordingly, a camera 72a is configured to acquire images of the weld zones of product units PU in the continues web W, while the camera 72b is configured to acquire images of the weld zones of the cut product units CU. In general, the camera 72 may thus be placed at any (fixed) position within the production line, which permits to acquire images of the weld zones to be monitored. However, in case the web W comprises at least in part elastic portions, such as the regions 205 and 215 shown in FIG. 3, it is preferable that the camera 72 acquires images of the continuous web W upstream the cutting station 50.

As shown in FIG. 2, in order to correctly acquire images of the product units PU/CU and in particular the respective weld zones to be monitored, the processing unit 70 and/or the camera 72 may receive a synchronization signal SYNC. For example, this synchronization signal SYNC may correspond to a trigger signal indicating when a product unit PU/CU reaches a given position within the production line. For example, the synchronization signal SYNC may be generated based on the advancement/velocity of the web W or a conveyor belt transporting the cut units CU. For example, such synchronization signals are conventionally used by a programmable logic controller (PLC) controlling at least part of the operations of the production line.

Additionally or alternatively, the camera 72 may have a frame rate being sufficient high in order to acquire plural images while a product unit is passing through the image area of the camera 72. In this case, the processing unit 70 may be configured to determine the weld area(s) in the images via image processing operations.

Similarly, the image acquired by the camera 72 may also contain a larger area of the product unit or even the complete product unit. In this case, the processing unit 70 may be configured to crop the image to a given sub-area within the image. Specifically, in various embodiments, the dimension of the sub-area may be fixed/predetermined. For example, in a currently preferred embodiment, the sub-area corresponds to a rectangle. For example, knowing the size of the welding zone, the processing circuit 70 may calculate the size of the rectangle from the parameters of the camera 72, for example, the focal length and the distance from the product units. Alternatively, the size of the rectangle may be set by an operator, e.g., via a graphical user interface of the processing system 70.

As mentioned before, the position of the sub-area/weld area may be either fixed (e.g., in case the images are acquired in response to a synchronization signal SYNC) or determined automatically, e.g., via image processing operations which determine the position of given characteristic elements within the image.

Generally, such a larger image may also be acquired via a line-scan camera, wherein the processing unit 70 may generate a larger image by sequentially adding the image lines provided by the line-scan camera.

For example, in various embodiments a monochromatic camera DALSA GENIE NANO M4030 or M4060 may be used as camera 72.

As shown in FIG. 2, in various embodiments, the web W or the cut units CU may be retro-illuminated by a uniform light source 74, such as light source 74a for the camera 72a and a light source 74b for the camera 72b. For example, also in this case, it is preferable that the images are acquired of the web W via the camera 72a, because the web W may pass the light source 74a without a conveyer belt. Alternative a transparent conveyor belt may be used. For example, in various embodiments, the light source 74 may be a backlight PHLO LEDW-BL-200X200.

Figure 4:
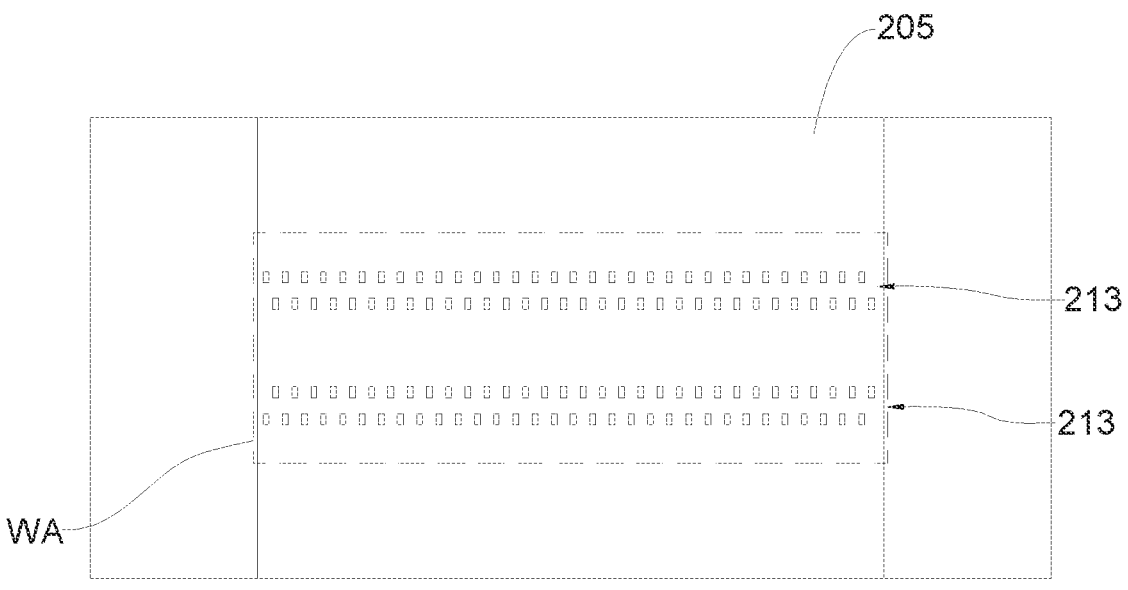
FIG. 4 show an example of an image of the weld areas generated by the production line of FIG. 2.

FIG. 4 shows in this respect schematically a possible image of the area of the region 205, in particular near the cut area 204, where the two welding lines 213 are placed. Specifically, in the example considered, the web W would indeed be dark, because the web W is retro-illuminated, whereby the regions not covered by the web W and the weld spots of the welding lines 213 would be shown with a higher luminosity.

As mentioned before, the images may then be pre-processed, e.g., in order to convert the images, crop the images to a weld area WA, etc.

Figure 5A:
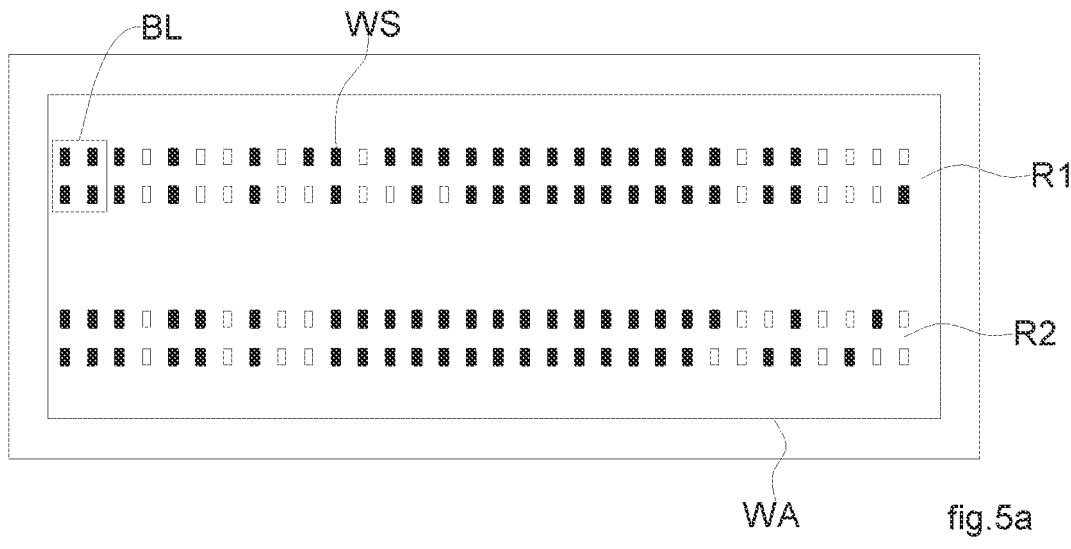
FIGS. 5A, 5B and 5C show examples of pre-processed images of weld areas generated by the production line of FIG. 2.
Figure 5B:
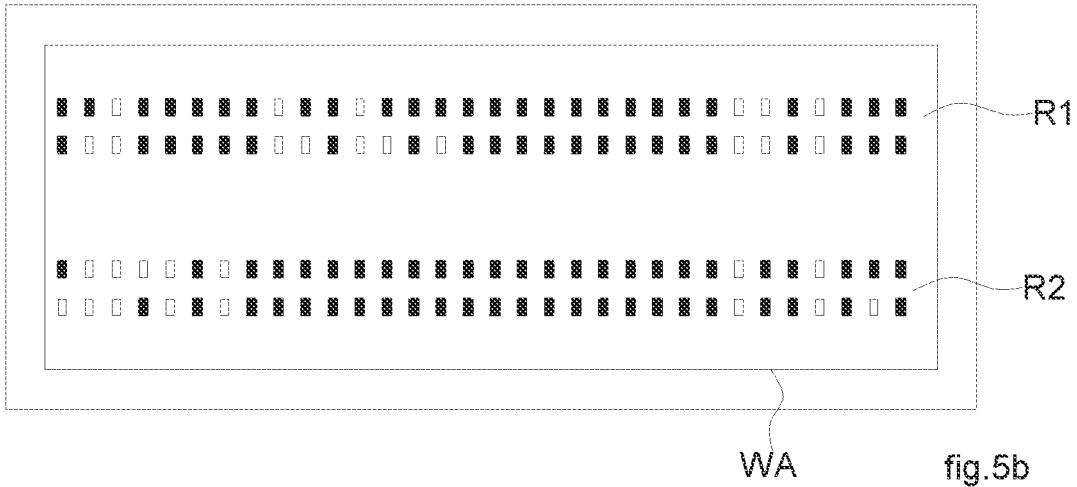
Figure 5C:
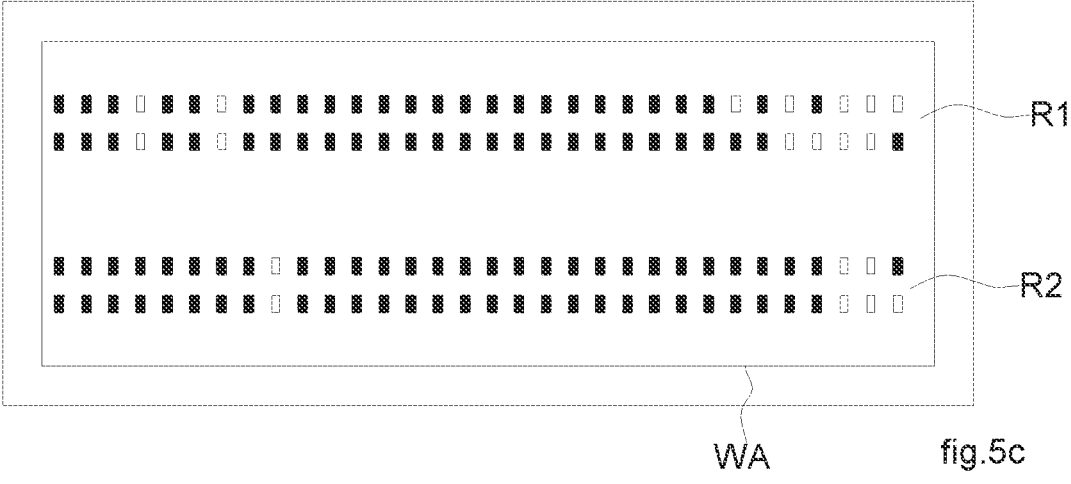

For example, FIGS. 5A, 5B and 5C show schematically examples of images of the weld area WA relating to three different product units. In order to better highlight the weld spots, these images essentially represent negatives of the images acquired by the camera 72.

Specifically, in the embodiment considered, the weld area WA comprises two rows R1 and R2 of weld spots WS, e.g., corresponding to the welding lines 213 described in the foregoing. Each row R1/R2 comprises blocks BL of a given number of weld spots WS, such as four weld spots WS, wherein the blocks BL are repeated a given number of times, e.g., repeated 16 times.

Specifically, as mentioned before, in various embodiments, the weld area WA relates to the weld spots WS in an elastic or at least partially elastic composite material, such as the regions 205 and 215. For this reason, due to the elastic behaviour of the composite material, the rows R1/R2 may not be perfectly linear, and also the distance between the weld spots within a block BL may vary. Again, for this reason, it is also preferable to acquire images of the continuous web W, because this effect is reduced.

However, this variability of the distribution of the weld spots WS (also of good products) implies that it is not easily possible to determine the quality of the complete weld area WA. Moreover, another major variability derives from the non-woven materials, such as the materials NW1 and NW2 (see FIG. 1). In fact, such materials do not have a uniform absorption profile, and the light intensity of the pixels may vary rather randomly between brighter and darker values For example, for this reason, it is not sufficient to just store a reference image of the weld area WA of a good product and compare the current image of the weld area WA of another product with this reference image.

Moreover, in the example shown in FIGS. 5A to 5C, the weld area WA comprises a total of 2×4×16=128 weld spots. However, from a practical point of view, indeed a product unit may have a sufficient quality even in case not all weld spots have been implemented perfectly.

For example, in this respect, the inventors have observed that the weld quality may be classified via the processing unit 70 by:

- detecting the weld-spots WS in the image, e.g., by determining areas in the pixel data having a given area between a minimum and a maximum value;
- determining the total area of the detected weld-spots WS;
- verifying whether the number of weld-spots WS is between a first lower threshold and a first upper threshold;
- verifying whether the total area of the detected weld-spots WS is between a second lower threshold and a second upper threshold; and
- classify the weld area WA as good, when the number of weld-spots WS is between the first lower threshold and the first upper threshold, and the total area of the detected weld spots WS is between the second lower threshold and the second upper threshold.

However practical experiments conducted by the inventors showed that the above solution based on thresholds is often not suitable, because either too many defective products are classified as good products or too many good products are classified as defective products. For example, this derives from the fact that the light intensity varies for the non-woven materials, wherein it is difficult to establish a fixed threshold for detecting the areas associated with weld-spots. Moreover, this approach does not take into account that a weld area having a single missing weld spot WS within each block BL may still be a good product, while a sequence of blocks BL having all weld spots WS missing may already have an insufficient quality. However, the above threshold method does not take into account the location of the defect.

Figure 6:
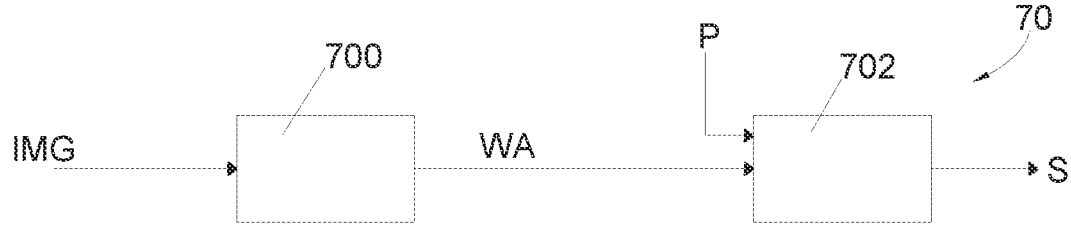
FIG. 6 shows an embodiment of a processing system configured to determine via a classifier a welding quality as a function of the pixel data of the images shown in FIGS. 5A, 5B and 5C.

FIG. 6 shows thus an embodiment based on a different approach. In particular, in the embodiment considered, the processing circuit 70 processes, as described previously, in a pre-processing step/block 700 the images supplied by the camera 72 to determine the pixel data of the image associated with the weld area WA.

In various embodiments, the pixel data of the weld area WA are then supplied to a step/block 702 configured to classify the status S of the weld area WA as a function of the pixel data of the weld area WA. In particular, in various embodiments, the classifier of step/block 702 is implemented with a machine-learning method. Accordingly, the pixel data of the weld area WA essentially correspond to the features/input data of the machine-learning method.

In general, the step/block 702 may also use other features, such as process parameters P, e.g., including:
  one or more parameters of the welding station 10 having generated the weld spots WS in the weld area WA, such as the velocity of advancement of the product unit in the welding station, one or more parameters of the welding element 18, etc.; and/or
  a product type parameter identifying the type of the product or the specific weld area WA, which will be described in greater detail in the following.

Figure 7:
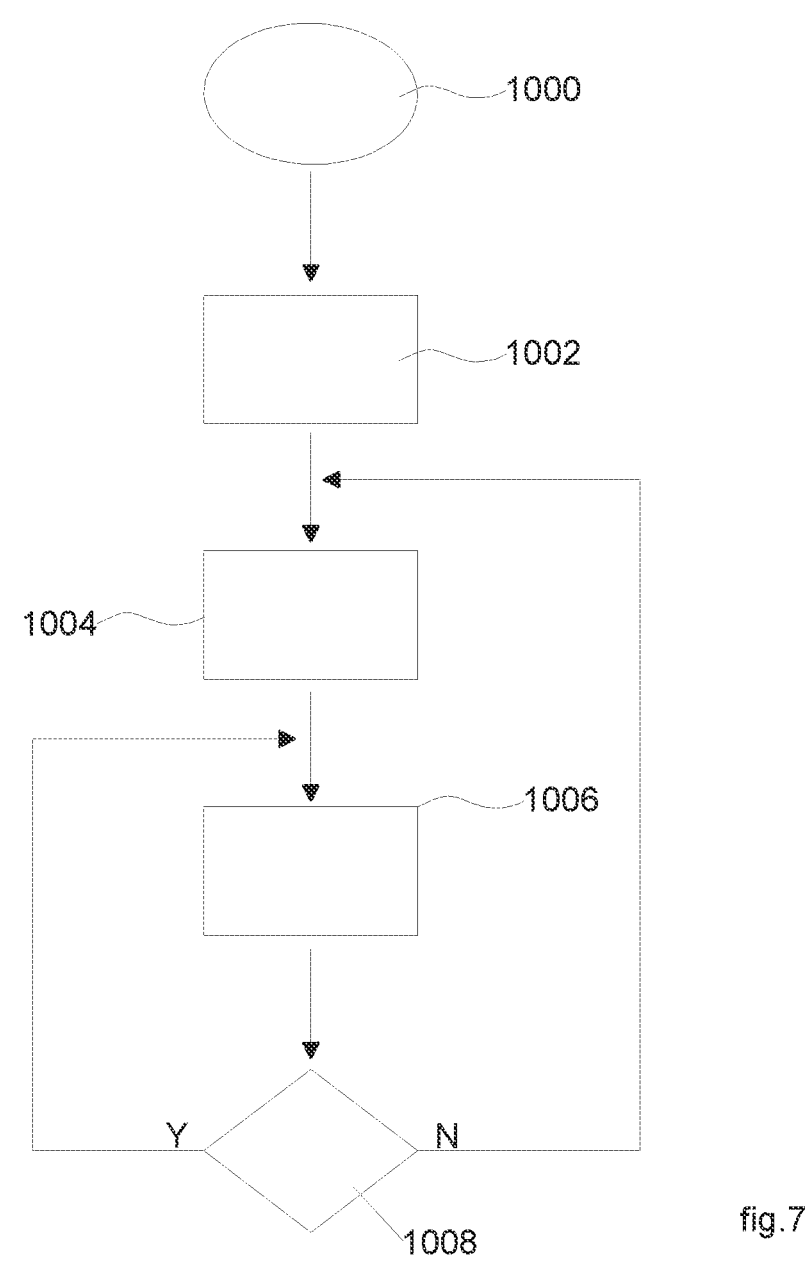
FIG. 7 shows an embodiment for training and use of the classifier of FIG. 6.

In particular, as illustrated in FIG. 7, after a start step 1000, the processing circuit 70 monitors, in a learning step 1002, a plurality of welding operations. In particular, for this purpose a plurality of welding operations are carried out under different welding conditions. For instance, for this purpose:
  the power supplied to the welding element 18 may be varied; and/or
  the speed of advance of the web W within the welding station 10 may be varied; and/or
  the welding zone WA may be contaminated, for example with splashes of water and/or dust; and/or
  the pressure between the welding element 18 and the anvil 16 may be varied, for example by varying the gripping force.

Next, an operator can verify the weld quality. For instance, the operator can carry out mechanical tests (for example, tests on the strength of the connection between the various layers of the composite material) and the operator can classify the weld quality as sufficient (for example, S=1) or insufficient (for example, S=0). In general, one or more of the tests used in this step may also be destructive. For example, the mechanical tests may include a tensile test in which the tensile force applied is increased until the layers of the composite material detach in the weld area WA.

For example, FIG. 8 shows an embodiment of a training pant, representing the cut product unit CU, implemented with the process described with respect to FIG. 3, wherein the web W is folded and then the welding lines 213 are applied before the web W is cut between two consecutive welding lines 213. Accordingly, in the embodiment considered, the welding lines 213 represent the side seals of the training pant in order to connect the regions 205 and 215.

For example, in order to perform repeatable test on a plurality of products, the operator may cut the side seals near the weld-area in order to obtain stripes/samples, e.g., of 1 inch width. For example, as shown in FIG. 9A, the operator may obtain in this way three samples of the left weld area and three samples of the right area, i.e., a total of six samples. Specifically, as shown in FIG. 9B, due to the fact that the regions 205 and 215 are only joined via the welding lines 213, each sample comprises a portion/wing of the layer 205 and a portion/wing 205 of the layer 215, which are not joined via the welding line 213. Accordingly, these portions/wings may be clamped into a tension testing device in order to test the mechanical connection between the layers 205 and 215 in the welding area. For example, the tester may be from Instron using the following tester settings:
  crosshead speed: 300 mm/min;
  max elongation: break load;
  jaw space interval: 25 mm;
  sample width: 1 inch.

For example, the weld quality may be classified as insufficient, when the two layers 205 and 215 are separated in the seam area during the test.

Consequently, the data acquired in the step 1002 represent a training dataset, which comprises experimental data both for conditions where the weld area WA has a sufficient quality and for conditions where the weld area WA has an insufficient quality.

Consequently, during a training step 1004, the processing circuit 70 may train the classifier 702 using the features F, in particular the pixel data of the weld area WA, as input data of the classifier 702 and the weld status S as output of the classifier 702. In general, different classifiers of the supervised-machine-learning category may be used, such as artificial neural networks or support vector machines.

For example, in a currently preferred embodiment, the processing unit 70 uses at the step 702 a Convolutional Neural Network (CNN). Convolutional Neural Networks are per se known, as evidenced, e.g., by the corresponding web page on Wikipedia® https://en.wikipedia.org/wiki/Convolutional_neural_network.

For example, in the context of a CNN, the inventors have observed that the processing system 70 may execute at the pre-processing step 700 a normalization operation, where the processing system 70:
  optionally (in case the pixel data are colour data) converts the pixel data of the weld area WA into grey scale pixel data, e.g., having values between 0 and a maximum value, e.g., 255; and
  normalizes the grey scale pixel data by scaling the pixel data, e.g., to a range between 0 and 1, e.g., by dividing the value of the grey scale pixels by a maximum value of the pixel data.

Generally, the value 0 may correspond to a black pixel or a white pixel. Specifically, the inventors have observed that the value 1 should preferably be associated with the colour of the weld spots WS in the weld area WA, e.g., black in FIGS. 5A to 5C. For example, the weld areas WA shown in FIGS. 5A to 5C may have 600×130=78000 pixels, each comprising a value between 0 and 1.

Figure 10:
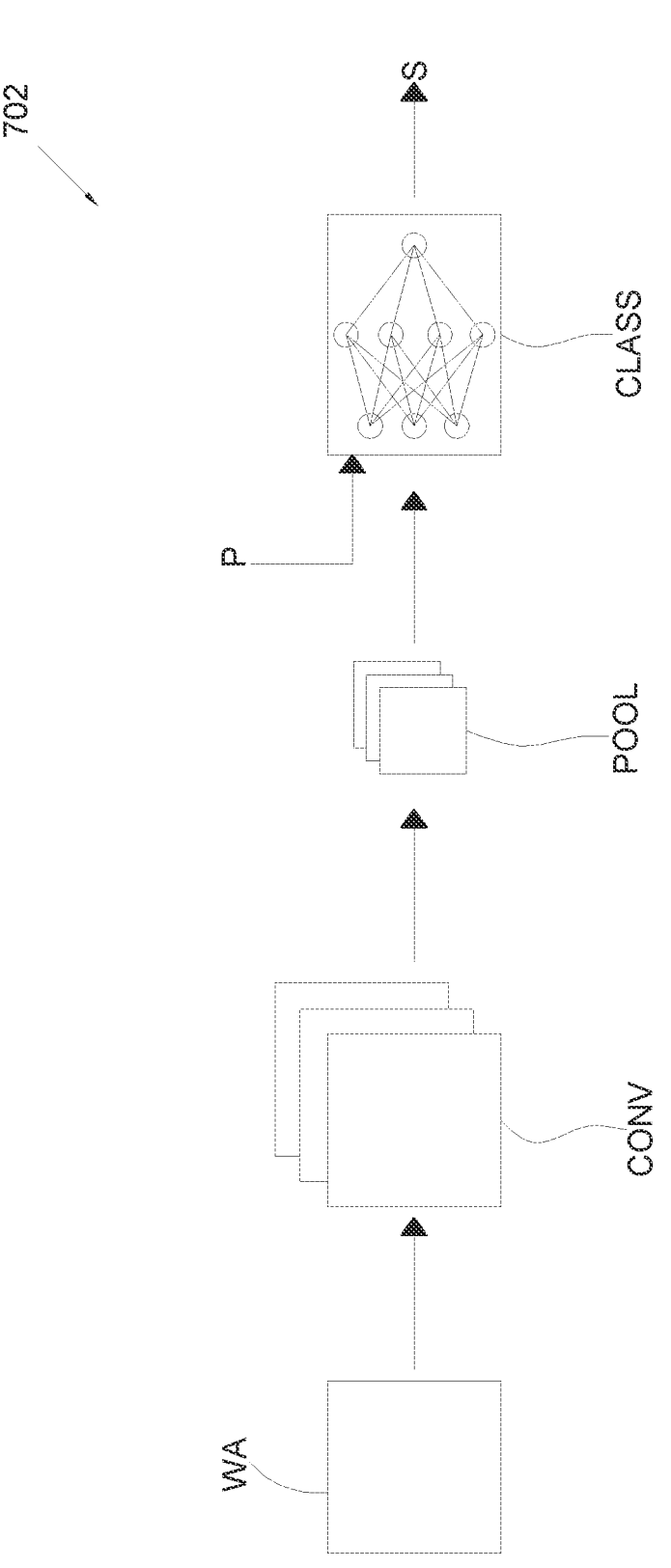
FIG. 10 shows an embodiment of the classifier of FIG. 6.

Accordingly, in various embodiments and as also shown in FIG. 10, the CNN comprises an input layer corresponding to the pixel data of the weld area WA, e.g., the normalized pixel data (e.g., 78000 pixel values).

In various embodiments, as usual for CNNs, the input layer is followed by one or more convolutional layers CONV, which perform a parameterized convolutional operation of the pixel data received. Specifically, compared to a conventional Artificial Neural Networks (ANN), usually the convolutional layers receive locally connected features, such as an array of pixels, e.g., 3×3, 5×5, 7×7, etc. pixels. Substantially, such convolutional layers CONV act as a feature extractor of graphical features. In various embodiments, a convolutional layer CONV comprises or is followed by a respective ReLu layer, which applies an activation function to the values calculated by the convolutional layer, e.g., in order to set negative values to zero.

Generally, each convolutional layer CONV does not comprise necessarily a single convolutional filter layer, but the convolution layer CONV may comprise a plurality of convolutional filter instances, which provided at output a so-called "volume" having a given depth (as schematically shown in FIG. 10).

Moreover, each convolutional layer CNN is following by a pooling layer POOL, which performs a down-sampling. Thus, essentially, the dimension of the feature space is reduced sequentially.

Finally, the last pooling layer POOL is followed by a classification layer CLASS. For example, in various embodiments, the classification layer CLASS comprises a fully connected layer receiving the data from the previous pooling layer POOL, which thus represent the input features of the classification layer CLASS.

In various embodiments, the classification layer CLASS comprises moreover a feed-forward ANN comprising one or more hidden layers configured to classify the input features of the classification layer. For example, each layer of the ANN may be implemented with a weighted sum and a suitable activation function. Generally, the classification may also be implemented with other classifiers, such as a Support Vector Machine (SVM). In various embodiments, the classification layer CLASS may also receive as input feature one or more of the optional features P mentioned in the foregoing.

Accordingly, in various embodiments, an output node S of the CNN, i.e., the classification layer CLASS, may provide a continuous value in a range between 0 and 1, which is indicative of the weld quality. Accordingly, a hard decision may be taken by comparing the continuous value with a threshold value in order to indicate whether the weld quality is sufficient (e.g., S=1) or insufficient (e.g., S=0). The output of the classifier 702 may in any case correspond to a continuous value, for example in the range between 0 and 1, which indicates the confidence of the estimate.

Accordingly, the CNN essentially corresponds to a parameterized mathematical function, wherein each node is characterised by the respective parameters, in particular the convolution parameters of the convolution layer(s) CONV and the weights of the classifier CLASS. Accordingly, during the training phase, the processing unit 70 may adjust these parameters via an iterative training process. Generally, the training of CNNs is per se well known in the art.

Consequently, at the end of the step 1004, the classifier 702 is able to estimate the quality of a weld area WA as a function of a set of features F including the (normalized) pixel data of the weld area WA.

Then, once step 1004 is completed, the production line may be used during a normal operating step 1006, where the weld quality is estimated without any further checks via an operator.

Consequently, in step 1006, the processing circuit 70 again monitors the weld areas WA of the product units, determines the features F, and uses the trained classifier to estimate the weld status/quality S as a function of the features F for the current weld area WA (see also the description of step/block 702).

In general, an operator can in any case carry out further tests for verifying the weld quality, as described with reference to step 1002. For instance, this may be useful during the initial step of development of a new welding process in such a way as to verify the estimate made by the classifier 702 and/or to carry out periodic monitoring of the results of the estimation, for example to obtain additional data that have not been taken into consideration previously.

Consequently, as represented schematically in FIG. 7, in the case where the operator determines, in a verification step 1008, that the result of the classifier is correct (output "Y" from the verification step 1008), the process can continue with step 1006.

Instead, in the case where the operator determines, in the verification step 1008, that the result of the classifier is erroneous (output "N" from the verification step 1008), the operator can store the data of the weld area and the respective corrected quality in the training dataset and can restart the step 1004 for training the classifier again.

Consequently, in various embodiments, the data acquired during normal operation 1006 can themselves be used as training dataset. For instance, for this purpose, the processing circuit 70 may be configured, for example by means of an appropriate computer program, for storing the training dataset directly in the processing circuit 70 and managing, also directly, the training step 1004, thus enabling a new training of the classifier when the training dataset changes.

As mentioned before, in various embodiments, the processing system 70 may use at the step 702 a product type parameter. Specifically, modern production lines may often be used to produce different products, or simply the profile of the weld spots WS in the weld area WA may be varied, e.g., by using a different anvil 16, thus implementing different weld patterns.

Accordingly, the product type parameter may represent an input parameter P of the classifier or preferably the product type parameter may be used to switch between different classifiers 702, both during the training phase and the normal operation phase.

In various embodiments, the production line may also comprise a rejection station 60 (see FIG. 2). Specifically, the processing unit 70 may be configured to drive the rejection station 60 as a function of the status S determined by the classifier 702, in particular in order to:

in case the quality of the weld area WA has been classified as good, drive the rejection unit 60 such that the respective cut product unit CU bypasses the rejection station 60 or generally proceeds into a first direction associated with good units GU; and in case the quality of the weld area has been classified as insufficient, drive the rejection unit 60 such that the respective cut product unit CU is deviated into a rejection bin 62 or generally proceeds into a second direction associated with bad units BU.

Generally, for this purpose, the processing unit 70 may be configured to track the position of each product unit within the production line, at least once the image of a given product has been acquired and the weld quality of the respective unit has been classified. This applies both in case the product unit PU is still part of the web W and in case the product units have already been separated into the units CU.

Solutions for tracking products within a production line, e.g., based on the advancement/velocity of a conveyor belt, are per se well-known in the art.

Additionally or alternatively, the processing unit 70 may be configured to generate a warning signal when the welding quality of a given number of consecutive product units has been classified as insufficient. In fact, this condition typically indicates a malfunction of the corresponding welding station 10. Generally, the warning signal may be provided to a visual and/or acoustic signalling device, and/or used to automatically stop the production line.

Additionally or alternatively, the processing unit 70 may be configured to adapt one or more parameters of the welding station 10, such as the power supplied to the welding element 18.

Generally, the inventors have observed that the described solution may also be used to test other characteristics of such absorbent sanitary articles.

Specifically, the inventors have observed that the described solution may also be used to classify the quality of other characteristics which may be observed in the retro-illuminated images.

For example, this applies to the absorbent layer 202. For example, in this case, the defects are usually associated with areas having a reduced density of the absorbent material, and such defects result in areas having overall higher luminosity values. However, also in this case, the position and strength of the variations may be relevant in order to classify the overall quality of the absorbent insert 202. Moreover, the non-woven materials may introduce random variations in the grey-scale images obtained of the absorbent layer 202.

Accordingly, similar to the process described with respect to FIG. 7, the processing unit 70 may be configured to monitor the absorbent insert 202 via the camera 72, wherein the camera 72 provides a sequence of images, and wherein a given area of the pixel data of the images corresponds to the absorbent insert 202. For example, in the case of training pants, the images should be acquired before the continuous web W is folded.

Accordingly, also in this case, images may be acquired during a learning step 1002 both for absorbent inserts 202 with a sufficient quality and with an insufficient quality. For example, in order to classify the quality of an absorbent insert 202 during the learning step, an operator may execute the so-called Hardy Integrity Test (HIT). Substantially, during the Hardy test, the sanitary product is subjected to a series of drops from a given height until the absorbent insert loses at least in part its structure.

Additionally or alternatively, by adopting a suitable camera 72, also the distribution of a Super Absorbent Polymer (SAP) within SAP absorbent inserts 202 may be classified. For example, the distribution of the SAP material may be visible in hyperspectral images, and/or images obtained via infrared spectroscopy (FTIR) and/or X-ray diffraction (XRD).

For example, in order to classify the quality of SAP distribution during the learning step, an operator may perform tests with a bromocresol solution according to the SAP.3001.1 test method.

Next, during a training step 1004, the pixel data may be processed for training a classifier 702, such as a CNN, configured to estimate a quality of the absorbent insert 202 as a function of respective pixel data of the absorbent insert 202. Finally, during a normal operating step 1006, the processing unit 70 may monitor via the camera 72 an absorbent insert 202 and estimate via the classifier 702 the respective quality.

For example, the inventors have observed that in the case of absorbent inserts 202, the dimension of the images may be significantly reduces compared to the classification of welding spots, because the respective defects are usually associated with larger areas.

Of course, without prejudice to the principles underlying the invention, the details of construction and the embodiments may vary widely with respect to what has been described and illustrated herein purely to way of example, without thereby departing from the scope of the present invention, as defined by the ensuing claims.

The invention claimed is:

1. A method of analysing a quality of a welding area of an absorbent sanitary article, said welding area being generated by a welding station of a production line by generating a plurality of welding spots in said welding area according to a welding pattern, the method comprising the steps of:
   monitoring said welding area via a camera and a processing unit operatively connected to said camera, wherein said camera provides a sequence of images, and wherein a given area of pixel data of said images corresponds to said welding area;
   during a learning step, wherein a plurality of welding operations are performed under conditions resulting in at least one welding area of sufficient quality and with at least one welding area of insufficient quality, monitoring via said camera the welding area generated for each welding operation of the plurality of welding operations;
   during a training step, processing via said processing unit the images of said welding areas monitored during said learning step to determine for each image a given area of the pixel data corresponding to the welding area and for training a classifier of the processing unit using the respective pixel data of the respective weld area as input data of the classifier and a weld status as output of the classifier, whereby the classifier is configured to estimate a welding quality in the welding areas as a function of the respective pixel data of the respective welding area; and
   during a normal welding operating step, monitoring via said camera the welding area generated by the welding operation and estimating via said classifier of the processing unit, the respective welding quality.

2. The method according to claim 1, wherein said classifier comprises a convolutional neural network receiving at input said pixel data of the welding area and providing at output the respective welding quality.

3. The method according to claim 1, comprising:
   providing a plurality of classifiers, each classifier being associated with a different absorbent sanitary article and/or a different welding pattern, and
   selecting one of said plurality of classifiers as a function of a value indicating a currently used absorbent sanitary article and/or welding pattern.

4. The method according to claim 3, wherein said plurality of welding spots are generated via said welding station in an elastic or at least partially elastic area of said absorbent sanitary article.

5. The method according to claim 4, wherein said plurality of welding spots are generated via said welding station in an area of a composite material of said absorbent sanitary article, said composite material comprising two outer layers of a non-woven fabric and an elastic inner layer.

6. The method according to claim 1, comprising, following upon the normal welding operating step:
   verifying the welding quality;

comparing the welding quality estimated by said classifier with the welding quality verified; and when the welding quality estimated by said classifier does not correspond to the welding quality verified, training again said classifier using the pixel data of said welding areas monitored both during said learning step and during said normal welding operating step.

7. The method according to claim 3, comprising:

when the estimated welding quality indicates an insufficient quality of a given welding area, discarding the respective absorbent sanitary article.

8. The method according to claim 1, comprising:

when the estimated welding quality for a given number of consecutive welding areas indicate an insufficient quality of said given number of consecutive welding areas:

generating a warning signal, which is provided to a visual and/or acoustic signalling device, and/or stopping said production line.

9. The method according to claim 1, wherein said monitoring said welding area via the camera comprises acquiring grey-scale images of a retro-illuminated continuous web of a composite material.

10. A production line configured to produce absorbent sanitary articles, comprising:

a welding station configured to generate a plurality of welding spots according to a welding pattern in welding areas of a web of a composite material;

a cutting station configured to periodically cut said web, thereby providing said absorbent sanitary articles;

a camera configured to provide a sequence of images, wherein a given area of pixel data of said images corresponds to said welding area; and a processing circuit operatively connected to said camera, the processing circuit having a computer-program product configured to be loaded into memory of at least one processor and comprising portions of software code for implementing the steps of the method according to claim 1.

11. A computer-program product configured to be loaded into memory of at least one processor and comprising portions of software code for implementing the steps of the method according to claim 1.

* * * * *